United States Patent [19]
Gonatas

[11] Patent Number: 5,528,365
[45] Date of Patent: Jun. 18, 1996

[54] METHODS AND APPARATUS FOR IMAGING WITH DIFFUSE LIGHT

[75] Inventor: Constantine P. Gonatas, Somerset, N.J.

[73] Assignee: The Trustees of the University of Pennsylvania, Philadelphia, Pa.

[21] Appl. No.: 203,378

[22] Filed: Mar. 1, 1994

[51] Int. Cl.⁶ .............................. G01N 21/49; A61B 6/00
[52] U.S. Cl. .............................. 356/340; 128/665; 356/41
[58] Field of Search ........................ 356/41, 340; 128/665

[56] References Cited

U.S. PATENT DOCUMENTS 5,070,455  12/1991  Singer et al. ..................... 364/413.19
5,119,815   6/1992  Chance .................................. 128/633

OTHER PUBLICATIONS

Oda et al "Non–Invasive hemoglobin oxygenation monitor and computed tomography by NIR spectrophotometry" SPIE vol. 1431 Time–Resolved Spectroscopy and Imaging Tissue (1991) pp. 284–293. Copy 356/41.

K. M. Yoo, F. Lie, R. R. Alfano, *Optics Letters*, vol. 16, No. 14, p. 1068 (1991).
D. A. Banaron, D. K. Stevenson, *Science*, vol. 259, p. 1463 (1993).
J. Schotland, J. Haselgrove, J. Leigh, *Applied Optics*, vol. 32, p. 448 (1993).

*Primary Examiner*—Vincent P. McGraw
*Attorney, Agent, or Firm*—Duane, Morris & Heckscher

[57] ABSTRACT

Methods of imaging objects with diffused light. The methods preferably can comprise the steps of illuminating the object with a source of light which can be scattered by the object, collecting the scattered light with a detector from multiple positions surrounding the object, measuring a mean free path of photons scattered from the object from the collected scattered light, and determining a diffusion constant for the photons scattered from the object as a function of the measured mean free path, and determining in the transmission of the photons between the source and the detector as a function of the diffusion constant, thereby imaging the object. Methods and apparatus described herein efficiently image objects with diffuse light by taking into account source-detector orientation and boundary effects.

19 Claims, 7 Drawing Sheets

METHODS AND APPARATUS FOR IMAGING WITH DIFFUSE LIGHT

FIELD OF THE INVENTION

This invention relates generally to imaging of objects. More specifically, this invention relates to methods and apparatus for imaging objects using diffuse light.

BACKGROUND OF THE INVENTION

Techniques for imaging objects have been used for nearly a century in the medical arts for diagnosing and understanding the myriad diseases and maladies that afflict the human body. Imaging techniques have also found use in such diverse fields as radio astronomy, sonar, radar and other fields which require information about an object which is not readily visible to the naked eye and therefore not easily examined. Medical imaging techniques include, for example, X-ray imaging, positron emission tomography (PET), ultrasound imaging and the well known magnetic resonance imaging (MRI).

In all of the imaging techniques mentioned above, narrow band frequency radiation illuminates the object of interest to produce reflected or emitted radiation which is then gathered from the object by a detector. The reflected or emitted radiation is then processed by an imaging algorithm to obtain useful information about the object.

In medical applications, the use of ionizing radiation in imaging, for example with X-rays, involves significant health risks to a patient when the patient is exposed to the radiation for prolonged periods of time or in multiple imaging schemes. Furthermore, certain of these imaging techniques undesirably involve the use of invasive procedures which are both costly and painful. Yet other techniques such as MRI do not yield consistently useful clinical results.

There has thus arisen in the medical imaging art an interest in developing non-invasive, safe imaging techniques which can take advantage of the natural scattering of visible and infrared light through media containing objects to be imaged. Techniques using diffuse light could be used in conjunction with other imaging schemes such as X-ray imaging or MRI to produce highly useful clinical images for diagnostic purposes.

Much of the progress in imaging with diffusive light has focused on ballistic techniques using lasers. With these methods, an intense pulsed laser illuminates a sample. Time gating the earliest photons—those photons that have been scattered only a few times, while rejecting all other photons—permits mapping of optical absorption. This technique works best when the allowed time window is short and photons deviate the least from their "ballistic" trajectory. Unfortunately, the transmitted intensity of unscattered photons diminishes exponentially with increasing sample thickness.

Because of these limitations on ballistic imaging, it is difficult to obtain high quality images of relatively thick objects with low power lasers. Examples of ballistic imaging techniques are disclosed in K. M. Yoo, F. Lie and R. R. Alfano, *Optics Letters*, Vol. 16, p. 1068 (1991), and in D. A. Benaron and D. K. Stevenson, *Science*, Vol. 259, p. 1463 (1993).

A second technique in the prior art is optical phase modulation. This technique can locate single absorbers using low power, continuous wavelength lasers by creating photon density waves. Anomalous phase shifts due to a single absorber are readily interpreted; however for a more complicated object a general analysis is required.

One such example of obtaining a characteristic of an object with diffuse light is disclosed in U.S. Pat. No. 5,119,815, Chance. The Chance patent reports a solution of the diffusion equation for a homogeneous medium to obtain the mean optical absorption of the entire object. This is possible for the homogeneous medium because the long time limit of the logarithmic derivative of the detected intensity yields the absorption characteristics directly. Thus the absorption characteristics for uniform structures may be obtained with the methods and apparatus disclosed in the Chance patent. However, in reality objects are heterogeneous and the long time limit of the intensity does not reveal the structure of the object.

Still other attempts to image with diffuse light are disclosed in U.S. Pat. No. 5,070,455, Singer et al. In the Singer et al. system, light intensities are measured at many sensor positions (pixels), initial values of absorption or scattering coefficients are assigned at each pixel, and then a new set of intensities at each pixel is calculated. The calculated intensities are compared to the real intensities, and the intensity differences are used to generate a subsequent interaction of absorption or scattering values for each pixel.

The methods described in Singer et al. usually require many iterations since the absorption or scattering values may not converge rapidly. The methods described in Singer et al. utilize cumbersome Monte-Carlo statistical techniques which consume large amounts of processing time without guaranteeing computational success. Singer et al.'s methods may also produce false local minima providing misleading results for the absorption characteristics.

Thus prior techniques using diffuse light for scattering fail to solve a long-felt need in the art for robust imaging techniques which can produce reliable images in biological systems. Solution of the aforementioned problems has heretofore eluded the medical imaging art. The inventor of the subject matter herein claimed and disclosed has recognized that solution of the diffusion equation to obtain images would solve these problems and fulfill the long-felt need in the art for an effective clinical tool in medical imaging.

SUMMARY OF THE INVENTION

The above described needs are met with methods, systems and apparatus provided in accordance with the present invention. In a preferred embodiment, methods of imaging an object with diffuse light are provided. The methods preferably comprise the steps of illuminating the object with a source of light which can be scattered by the object, collecting the scattered light with a detector from multiple positions surrounding the object, determining a diffusion constant for the photons scattered from the object as a function of the measured mean free path, and determining a net transmission of the photons between the source and the detector as a function of source-detector locations, thereby imaging the object.

Systems for imaging objects with diffuse light are also provided in accordance with the present invention. The systems preferably comprise a source which produces light to be scattered by the object, a detector for measuring light emitted from the source and scattered by the object, and processing means interfaced with the detector for determining net transmission of photons scattered from the object and detected by the detector, the processing means adapted to determine the net transmission as a function of a probability of photons hitting the detector after being scattered by the body.

The methods, systems and apparatus disclosed and claimed herein solve a long-felt need in the art for imaging objects with diffuse or scattered light. Without intending to be bound by any theories or postulates, the inventor has recognized that comparing the spatial distribution of photons scattered by an object to the flux calculated if the object were homogeneous yields the optical structure of the object being imaged convolved with a computationally tractable probability weight which describes the photon field within the object. By deconvolving the calculated probability weighting function from the data, a tomographic map of the optical absorption of the object can be obtained, thereby imaging the object. Such images have heretofore not been achievable with prior methods of diffusion imaging and evince startling and unexpected results when methods and apparatus provided in accordance with the present invention are employed.

The inventor has also discovered that photon current is anisotropic and therefore the photon flux must be measured paying particular attention to the detector orientation relative to the light source. It was not previously appreciated by those with skill in the art that imaging with diffuse light was sensitive to detector orientation. Comparing the photon flux in the inhomogeneous object with the detector in a given orientation with respect to the source, to the photon flux measured or calculated for a homogeneous object with the detector in the identical orientation is a more preferred mode of operation. This gives results superior to operations where detector orientation is not taken into account.

Importantly, methods and apparatus for imaging with diffuse light in accordance with the present invention provide computationally economic solutions for images of large objects with highly diffusive photons. Furthermore, imaging objects found within inhomogeneous media in accordance with the present invention is possible using low power sources such as lasers. This makes imaging techniques described herein particularly attractive for biological and medical applications.

The invention will be better understood with reference to the following detailed description read in conjunction with the drawings which are first briefly described below.

DETAILED DESCRIPTION OF PREFERRED EMBODIMENTS

Figure 1:
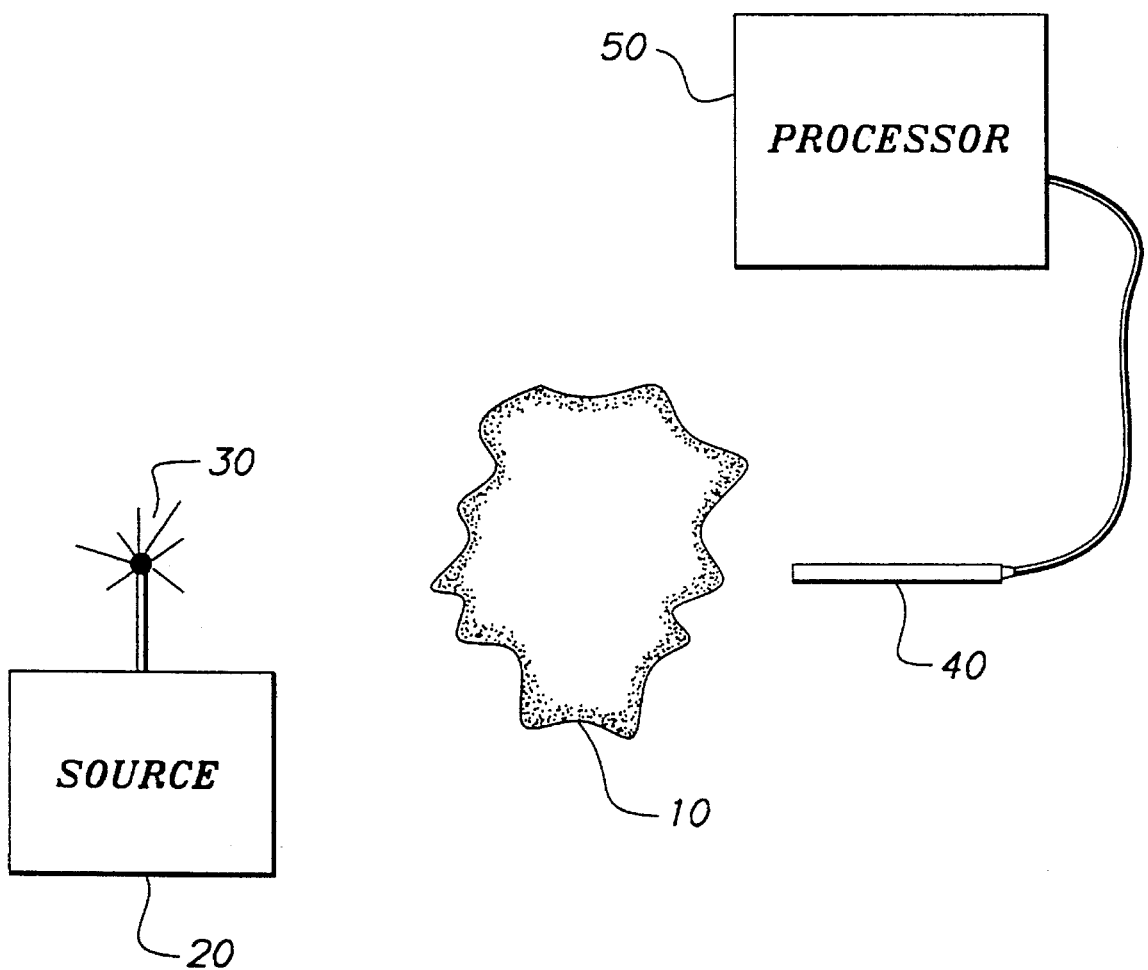
FIG. 1 is schematic diagram of an imaging system provided in accordance with the present invention.

Referring now to the drawings wherein like reference numerals refer to like elements, FIG. 1 shows a generalized imaging system using diffuse light to provide an image of object 10. Object 10 scatters a directed beam from source 20, thereby producing diffuse light. Light 30 can be a single wavelength, or multiple wavelengths depending on the application in which the imaging system provided in accordance with the invention is utilized. A detector 40 collects the photons scattered by object 10, and forwards information concerning the photons in the form of digital data to a processor 50. The processor 50 constructs an image of object 10 with the appropriate processing circuitry and software found therein.

With systems shown generally in FIG. 1, light propagation can be measured through a multiple scattering medium and the scattering mean free path measured for different geometries of scatterers. The intensity of scattered light can then be used to determined the composition of the scattering medium and to further characterize objects in the scattering medium.

Generally, scattering media do not have spatially uniform scattering and absorption constants. Thus, a considerable degree of complexity exists in interpreting scattered light data. Current systems do not have the ability to provide consistent measurements of the effective mean free path of scattered photons. Furthermore, prior work in diffusive imaging has not adequately taken into account the relationship between the orientation of the source of the light with respect to the detector, nor have prior diffusive light imaging systems been able to effectively deal with varying object geometries.

The above effects have profound impacts on the distribution of photon path lengths after the photons have been scattered by the object. The inventor of the subject matter herein claimed and disclosed has discovered that the orientation of the detector relative to the source affects the transmitted flux. Furthermore, the appropriate boundary conditions in effect at the interface between a scattering medium and a medium in which photons propagate freely must be fully characterized in order to obtain an image of the object.

This has important implications on the desire for non-invasive techniques in biological imaging, since if a detector is placed outside of the medium, the photons will naturally cross the interface boundary. Thus, for biological and medical imaging, boundary conditions should be fully understood. In accordance with the present invention, imaging methods and systems efficiently handle boundary conditions or discontinuities at boundary interfaces.

Imaging with diffuse light in accordance with the present invention begins with an understanding of the diffusion equation. Photon density within a multiple scattering medium is described by the diffusion equation in the following form:

$$\frac{\partial u}{\partial t} = D\nabla^2 u - \mu_a c u,$$

where u is the density of photons, $\mu_a$ is the absorption coefficient, $D=cl^*/3$, known as the "photon diffusion constant", and c is the speed of light in the scattering medium. If the filling fraction of the scatterer is small, differences in photon phase velocity and energy transport velocity can be ignored. The effective mean free path $l^*$ describes the length scale over which scattering is isotropic and is related to the mean free path, l, by the relationship $l^*=l/(1-g)$ where g is the average cosine of the single particle scattering angle.

By gathering data from a system such as that shown in FIG. 1, solutions to the diffusion equation can be used to determine the average light absorption coefficient $\mu_a$ and the scattering mean free path $l^*$.

In order to obtain an image of the object, it is preferred to map the physical absorption and/or scattering constants. According to the present invention, the spatial distribution of photons scattered by an object is compared to the flux calculated if the object were homogeneous. This measured ratio is equivalent to the spatially inhomogeneous optical structure of the object convolved with a probability weight describing the photon field. The data can then be deconvolved using the calculated weighting function to obtain a tomographic map of optical absorption and an image of the object. In order to calculate the weighting function, it is necessary to know the average scattering mean free path $l^*$.

In addition, if sources of illumination are placed outside the scattering medium, it is necessary to determine the photon boundary conditions at the surface of the object. These determine photon propagation through the object.

To obtain the tomographic map, it is necessary to fully characterize the behavior of the scattered photons in the medium. As described above, photon propagation obeys the diffusion equation when the spatial scale, L, of a scattering chamber is many times the size of the photon effective mean free path $l^*$. The absorption $\mu_a(r)$ of the photons is a function of position, thereby representing the structure of the object. For convenience, define $\mu'_a(r)=\mu_a(r)-\bar{\mu}$, where $\bar{\mu}$ represents the mean absorption in the object. Thus, $\mu'_a(r)$ is the spatially fluctuating component of absorption.

A technique to solve the diffusion equation in the presence of a spatially fluctuating absorption, has been partially described in J. Schotland, J. Haselgrove and G. Leigh, *Applied Optics*, Vol. 32, p. 448 (1993) wherein the concept of "hitting density" is introduced. The hitting density, denoted $v(r;r_1,r_2,t)$, is the probability weight at position r for a photon travelling from source position $r_1$ to detector position $r_2$ in total travel time t. A photon may pass through r at any time between 0 and t. The net transmission, T, of photons at $r_2$ is then attenuated by the local absorption at r in proportion to the density v. Taking the natural logarithm of the net transmission, the following is obtained:

$$lnT = -\int v(r;r_1,r_2,t)c\mu'_a(r)d^3r, \tag{1}$$

$T=S/S_0$ where S is the transmitted flux through the scattered object, $S_0$ is the flux transmitted by a homogeneous object of the same geometry, and v represents the hitting density in the absence of spatially fluctuating absorption. It should be noted that the source-detector orientation can affect substantially the flux. The approximation implicit in the above equation has validity when the limit:

$$\int_\gamma \mu'_a(r) dr \ll 1, \tag{2}$$

where $\gamma$ denotes a typical path of a photon traversing the absorbing object.

To obtain $\mu'_a(r)$ as a function of T the solution to the forward problem stated by Equation (1) must be inverted. In accordance with the present invention, the method for calculating the hitting density is direct. Thus, there is no need for computationally expensive Monte-Carlo simulations or complicated recursive formulae. For the infinite geometry, an analytic form is used to calculate v:

$$v(r;r_1,r_2,t) = \frac{1}{4\pi D}\left(\frac{1}{|r-r_1|}+\frac{1}{|r-r_2|}\right)\exp- \tag{3}$$

$$(-\frac{1}{4Dt}((|r-r_1|+|r-r_2|)^2-(|r_1-r_2|^2)).$$

In a semi-infinite geometry, v is equivalent to the "banana" shaped photon field which is well known to those with skill in the art.

A general prescription for v is given by Schotland, Haselgrove and Leigh, who obtain:

$$v = \frac{1}{u(r_1,r_2,t)}\int_0^t u(r_1,r,t')u(r,r_2,t-t')dt'$$

where u denotes the 2-point Green's function uniquely determined by the geometry, boundary conditions, and diffusion constant.

The inversion of Equation (1) is aided greatly by discretization such that:

$$\mu'_a(r)_i = \sum_j \frac{v_{ij}(r^+;r_1,r_2,t)}{cdV}\times(-lnT_j(r_1,r_x,t)). \tag{4}$$

Thus, according to the above equation, the probability weight v can be recast into matrix form and a pseudo-inverse $v_{ij}^+$ obtained. Using singular value decomposition to obtain $v_{ij}^+$, the smallest eigenvalues are truncated or dampened. This reduces the propensity of $v_{ij}^+$ to amplify noise. In this notation, $\mu'_a(r)_i$ is a column vector of absorption coefficients, $T_j(r_1,r_2,t)$ is a column vector consisting of the flux ratios, and the pixel volume is denoted by dV. The discrete quantities $r_1$, $r_2$, and t are preferably concatenated to form a single row or column index.

Figure 2:
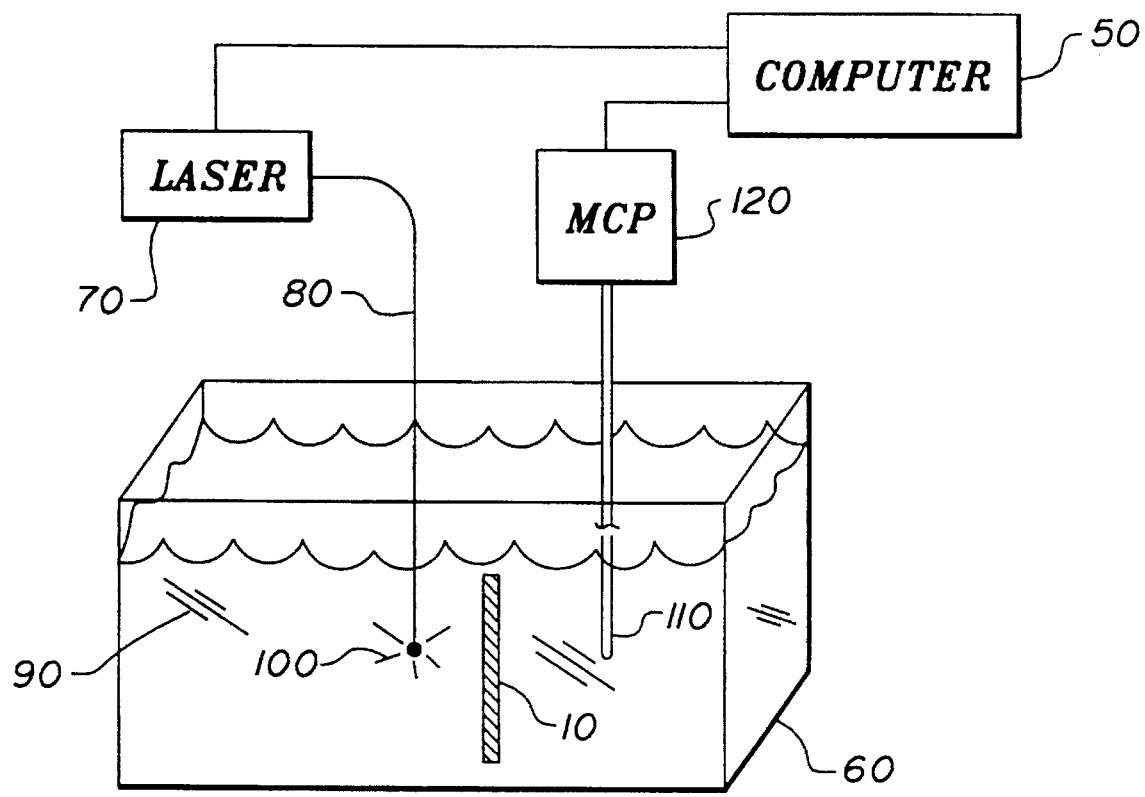
FIG. 2 is a schematic diagram of an experimental imaging system with which imaging of an object in an Intralipid scatterer was performed using diffuse light.

In a further preferred embodiment, the imaging system shown in FIG. 2 was constructed by the inventor and used to perform imaging tests in accordance with the present invention. A chamber 60 was constructed and filled with a 2% intralipid (IL) solution which in unadulterated form is a white liquid consisting of 20% soybean oil suspended in 80% water. The light source was a laser 70 which pulsed repeatedly at 5 Mhz. The pulsed 5 Mhz signal was injected via an optical fiber 80 into the chamber 60 through the IL shown generally at 90. The light 100 scattered through the IL was collected by a collector fiber 110 and detected by a detector 120 which in a preferred embodiment was a photomultiplier tube (PMT) manufactured by the Hamamatsu Company of Japan, Model No. R1517. Detector 120 alternatively could be a streak camera or microchannel plate detector. Computer processor 50 processed the data detected by the photomultiplier 120.

The laser pulses were 50 ps wide at 780 nm and the chamber 60 was a 20×20×40 cm tank containing the scattering IL suspension. The chamber was much larger than the largest separation between source and detector (6 cm). Thus, for excellent approximation the imaging experiment was performed in a free medium, with vanishing boundary conditions at infinity. The object 10 was one or more tubes containing IL of the same concentration as the ambient bath, together with a small quantity of ink. The scattered light was collected from multiple positions in the bath by fiber 110 and guided to the PMT 110.

Figure 3:
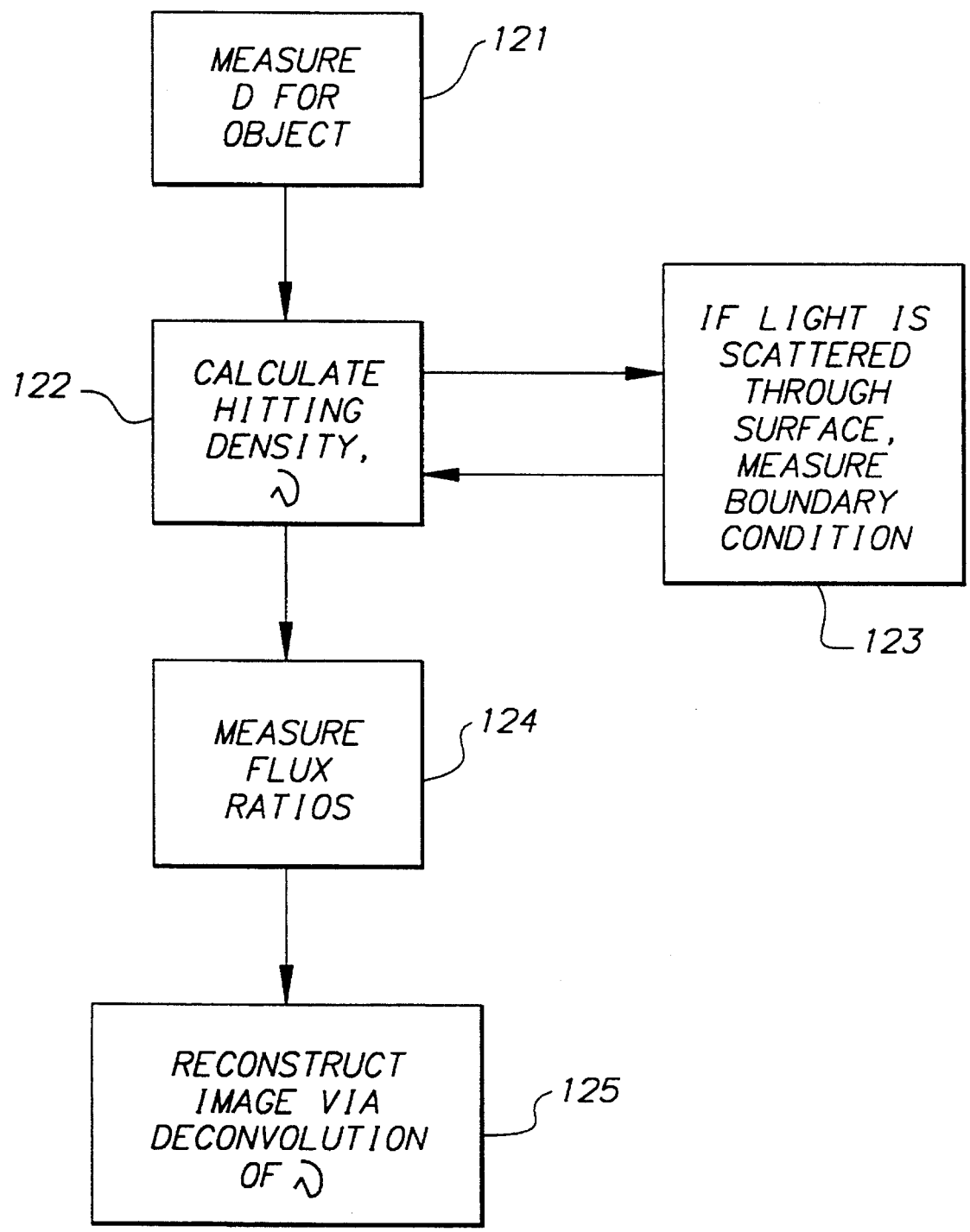
FIG. 3 is a block diagram of a generalized imaging method provided in accordance with the invention.

Generally, it is desired to measure the diffusion constant D for the object. In accordance with the invention, and as shown in FIG. 3, the generalized block diagram for performing this function is illustrated. At block 121, D is measured by solving the diffusion equation for the 2-point Green's function for the infinite geometry of the experiment which is given by:

$$u(r,t) = \frac{u_o}{(4\pi Dt)^{3/2}} \exp(-r^2/4Dt - \mu_a ct). \qquad (5)$$

Knowledge of the boundary conditions allow a determination of the 2-point Green's functions which, together with the geometry of the system, allow for determination of v. Furthermore, the detector orientation affects the observed fluxes J, which are not necessarily equal to the photon densities u. The relationship between the photon density, u, and the observed photon flux, J, is given by $$J_r = \frac{c}{4} \left( 1 - \frac{\hat{s} \cdot \nabla}{h} \right) u$$

where $h \equiv 3/2l^*$ and $\hat{s}$ is the unit vector along the source-detector axis. Alternatively, for the case where the detector is not inside the scattering medium but is placed at its surface, the photon density is equal to the photon flux, however the photon density is subject to the boundary condition $$uh + \frac{\partial u}{\partial z} = 0.$$

The inventor has realized a method for measuring the boundary parameter h, to be described hereafter. In the presence of a boundary, the photon density u is given by Equation (11).

Thus, by observing the flux for different positions r, it is possible to fit a single set of diffusion constants D and absorption constants $\mu_a$ for solution to the diffusion equation. Once this is accomplished at step 122, it is desired to calculate the hitting density v as defined above. At step 123, if light is scattered through the surface, it is then desired to measure the boundary conditions.

At step 124, it is preferred to then measure the net transmission function $T(t)=S(t)/S_o(t)$, where $S_o(t)$ is the transmitted flux in the absence of an absorber. Given the measured flux ratios, and the hitting density, it is then possible to reconstruct the image at step 125 via deconvolution of the hitting density from Equation (1).

To calculate v, it is preferred to first measure l* and determine D. In principle it is not necessary to measure $S_o(t)$, given $l^*, \bar{\mu}$ and the absolute detector sensitivity.

Figure 4A:
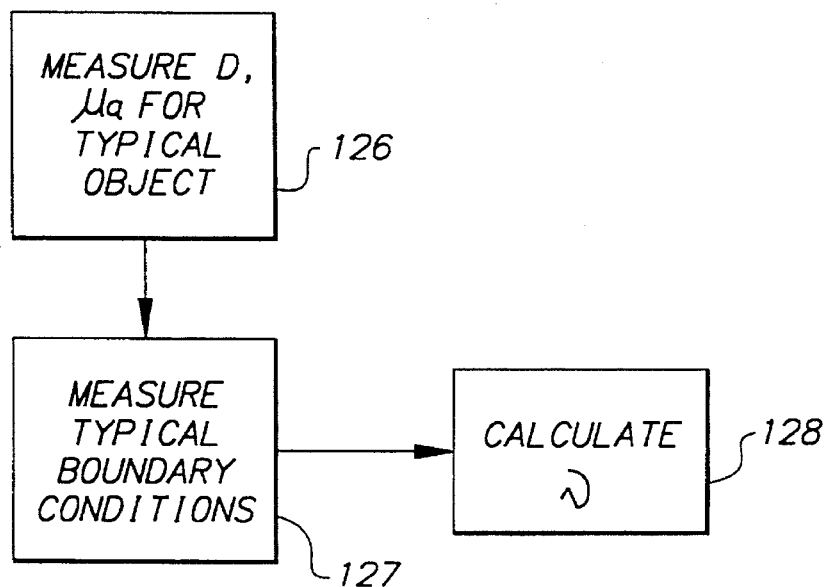
FIGS. 4A and 4B are block diagrams of an alternate imaging method which may be more practical with biological samples.
Figure 4B:
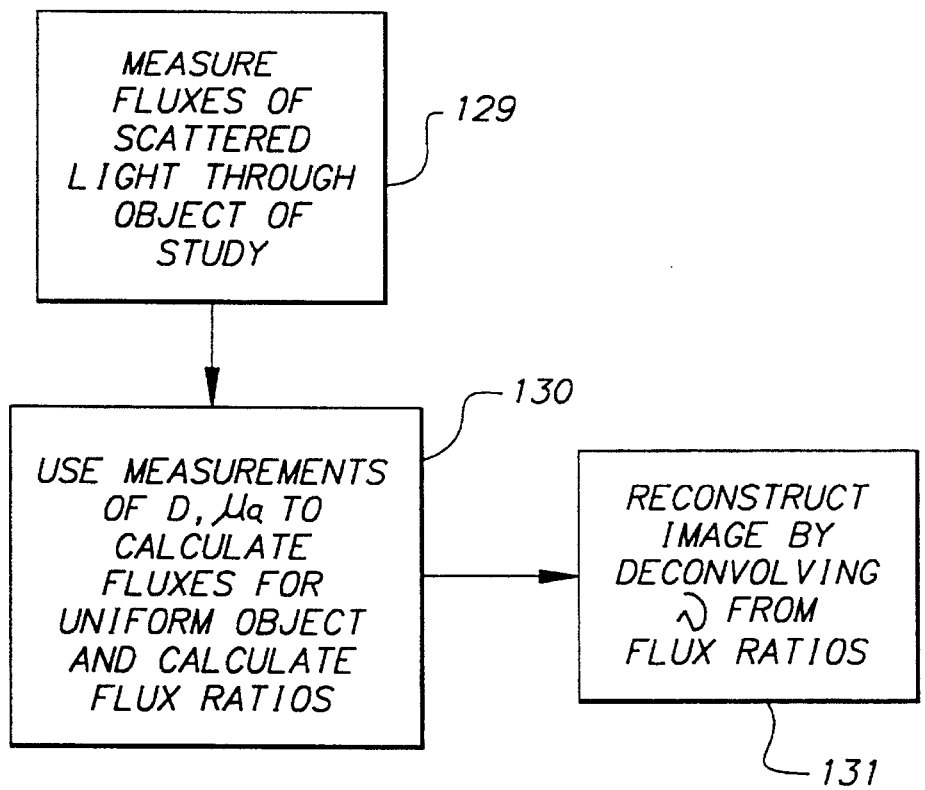

FIGS. 4A and 4B are a modified block diagram for imaging an object in accordance with the invention. As in the method described with respect to FIG. 3, at step 126 in FIG. 4A, D and $\bar{\mu}_a$ are measured for a typical object. In a preferred embodiment, using "typical" boundary conditions at step 127 allows absorbing or transmissive boundary conditions to be utilized to fully characterize the object. For example, to image a human breast or brain that may contain a tumor, it is not feasible to compare the scattered fluxes through the tissue to the fluxes through the same tissue with the tumor removed. It would be greatly desirable to know beforehand what the fluxes should be through tissue that is known to be free of tumors, or any other obstructions. Then, at step 128, it is possible to calculate the hitting density and image the object by deconvolution as discussed above.

In the second preferred embodiment, FIG. 4B illustrates an alternative imaging scheme wherein measured fluxes of scattered light through the object of study are first observed at step 129. This is not necessarily the same object as was discussed with respect to FIG. 4A at step 126, since it may not be practical to accomplish all the measurements required at step 126 to determine D and $\bar{\mu}_a$ for the object. However, at step 129 by observing measured fluxes, it is then possible to use previously determined D and $\mu_a$ to calculate the flux $S_o$ for the fiducial uniform object. It is then possible to calculate the flux ratios, and at step 131 to reconstruct the image by deconvolving v from the flux ratios. In accordance with the method of FIGS. 4A, and 4B (and for that matter, the generalized method of FIG. 3), accurate determinations can be made of the object by taking into account the boundary conditions.

Using the above analysis, a 1.4 cm diameter tube in an IL bath was examined wherein l*=0.3 mm. The tube was aligned along the z axis and characterized by an absorption $\mu_a$=0.64 cm$^{-1}$. The reconstructed value for the absorption $\mu_a$ (for an object)=0.34 cm$^{-1}$.

For an IL bath where l*=0.5 mm containing three equally spaced tubes of 5.5 mm diameters, the tubes oriented at the top and right of the chamber were characterized by an absorption constant $\mu_a$=0.13 cm$^{-1}$. The bottom left tube was characterized by an absorption $\mu_a$=0.26 cm$^{-1}$. With imaging methods provided in accordance with the invention, $\mu_a$=0.15 cm$^{-1}$ and $\mu_a$=0.24 cm$^{-1}$ were measured respectively for the two sets of tubes.

Generally, the absorption characteristics determined for this second data set agree quantitatively with actual absorption. However, with respect to the first dataset, the size of the object which produced the first dataset and the absorption were both too large for the approximation of Equations (1) and (2) to hold.

The methods of optical diffusion imaging described above extract information from photons scattered many times in their trajectory from source to detector. Thus, methods in accordance with the present invention open the possibility of using low power lasers to study thick (L>10l*) samples. Within the limit that the absorption through a finite object is not too large, absorption coefficients can then be mapped quantitatively.

As discussed above in Equations (1) and (4) respectively, the effects of detector orientation and boundary conditions at an interface with a free medium play profound roles in obtaining accurate observed values of $\mu_a$. The inventor has discovered that photon density, u(r,t) can be characterized with respect to these effects so that accurate absorption characteristics can be determined.

The inventor has further recognized that the observed light picked up by the detector is not the photon density per se, but is the directional photon current, $J_r$, into the detector aperture. This current is given by Fick's law, as $J=-D\nabla=J_+$ $r-J_-$ and represents the net current only, not the directional current. The directional current represents the inward flow component perpendicular to the plane of the detector aperture. By transport theory, the resulting current is expressed as:

$$J_r = \frac{c}{4}(u - \nabla_r u/h) = \frac{c}{4}\left(1 - \frac{\hat{s} \cdot \nabla}{h}\right)u \quad (6)$$

where h is defined as 3/(2l*) and ŝ is the unit vector along the source-detector axis.

The physical interpretation of photon density described by Equation (6) is that the distribution of photons in the diffusion regime is anisotropic. Thus, u is the isotropic part of the photon flux, and the gradient term is the directional component. If there are no directional components, the photon distribution would be isotropic at every position, in which case there would be no tendency for photons to migrate outward from the source.

For a homogeneous infinite medium, the application of Equation (6) is particularly simple, and can be written as:

$$J = \frac{u_o c}{4(4\pi Dt)^{3/2}} \exp(-r^2/4Dt - \mu_a ct)\left(1 + \frac{r\cos\theta}{ct}\right), \quad (7)$$

where θ describes the inclination of the detector toward the source-detector axis.

Figure 5:
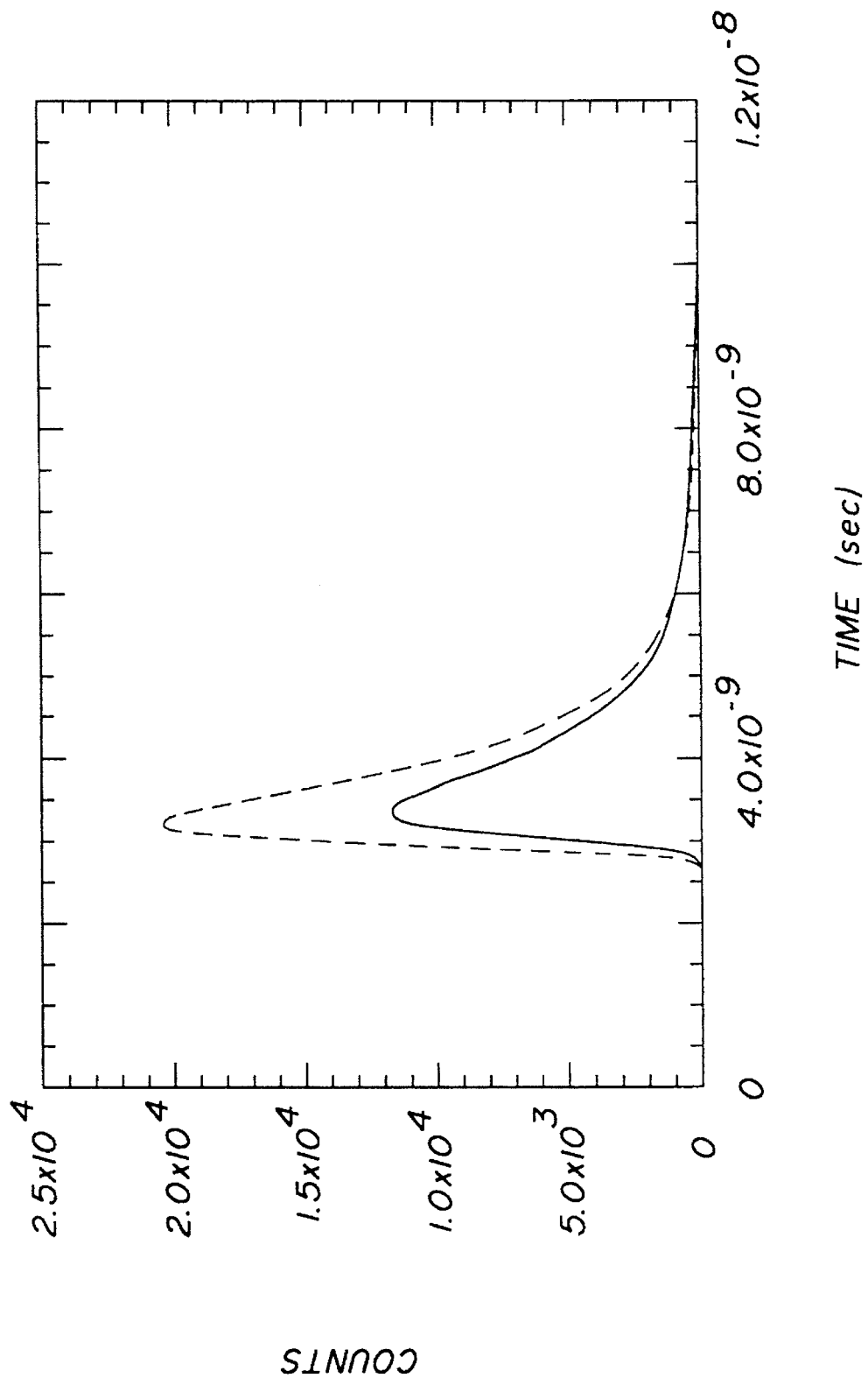
FIG. 5 is a graph of pulses propagating in 0.2% Intralipid scattering media. The solid line indicates data collected where a normal vector to the detector aperture is perpendicular to a source-detector axis ($\theta=\pi/2$), while the dashed line indicates data collected where the detector is facing the source ($\theta=0$).

By observing the photon current of Equation (7) with a system such as that of FIG. 2, the source-detector orientation can be taken into account and accurate images of an object obtained. Referring to FIG. 5, two pulses observed with the same source-detector separation but with the detector orientations corresponding to θ=0 and θ=π/2 are shown. It can be seen that with these two different detector orientations, a different photon current density is observed.

Figure 6:
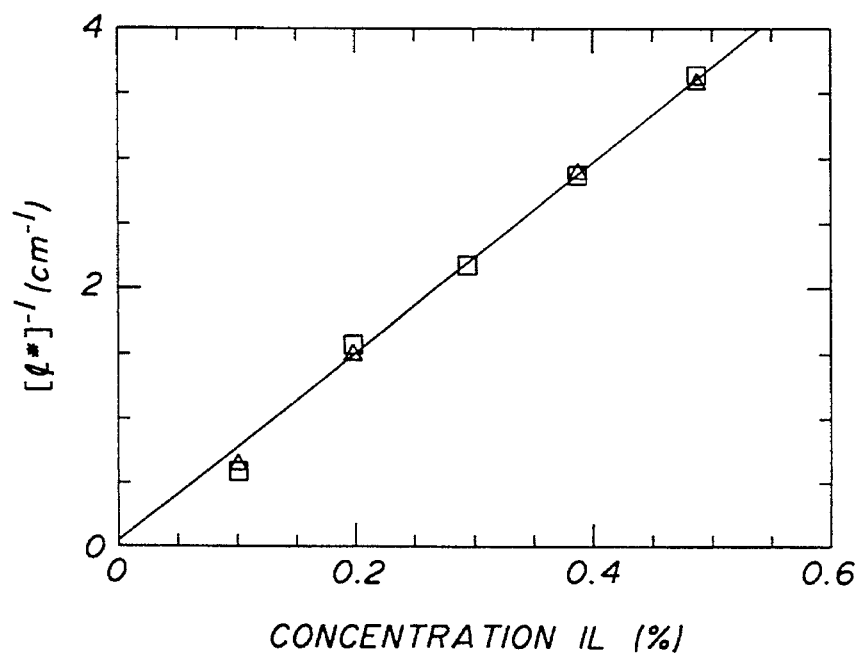
FIG. 6 is a graph of the reciprocal of the photon mean free path for different concentrations of scatterers where squares represent the detector perpendicular to the source and triangles represent the detector facing the source.

In FIG. 6, the scattering mean free path l*, determined separately for the detector in the θ=0 and θ=π/2 orientations is shown. The squares represent l* when θ=π/2, while the triangles represent l* when θ=0. The only significant deviation from a straight line fit is for the lowest dilution, in this case, the minimum ratio of source-detector distance to mean free path, that is, L/l* approximately 2.5. In this situation, the diffusion equation is no longer applicable.

As mentioned above, consideration of boundary conditions at the interface with the free medium and the pulse propagation near the surface of the semi-infinite volume is also necessary to obtain accurate $\mu_a$ and l* characteristics. At a surface, z=0 and the scattering medium is divided from a medium in which light travels unhindered. By comparing backscattering data for light that is free to radiate from the surface to light that is absorbed everywhere except at the detector position, accurate $\mu_a$ and l* determinations can be made with systems shown in FIG. 2. Boundary conditions were then studied so that absorption constants could be determined and imaging accomplished.

The absorbing condition is preferably treated analytically by an image source with negative intensity at z=−l* together with the source at z=+l*. The measured photon current at the surface can then be given by:

$$J = \frac{u_o l^*}{(4\pi D)^{3/2} t^{5/2}} \exp[-(r^2 + l^{*2})/4Dt - \mu_a^* ct]. \quad (8)$$

A second preferred approach to photon diffusion across a plane surface is to adopt the boundary conditions inferred from transport theory and which we have been used to interpret directional currents. For the semi-infinite volume containing scatterers for all z<0, the directional current at the surface is $J_{-z}$=0. That is, no light that leaves the scattering medium returns. However, a finite density of photons is permitted for z=0 at the surface, and the boundary condition for this situation is:

$$uh + \frac{\partial u}{\partial z} = 0. \quad (9)$$

Interestingly, a subtle distinction exists between this case and the absorbing condition, u at z=0 equal to 0. The first statement is concerned with photon flux, while the second statement concerns photon number density. Thus, the second statement is an approximation that describes the photon density at positions sufficiently far from the surface, and is mathematically simpler. However, the first statement is more readily adapted to the case where there is a mismatch in the index of refraction between the scattering medium and the free medium. Such a mismatch may change the boundary conditions which in turn modifies the distribution of photon path lengths.

Therefore, if there are internal reflections at the interface, they may be described as an incoming current, J_, related to the outgoing current, J_+ by J_=RJ_+ where R is an effective reflection coefficient. This in turn is related to the boundary coefficient h by:

$$h = \frac{3}{2l^*} \frac{R-1}{R+1}. \quad (10)$$

Given the boundary conditions for a semi-infinite volume, the photon density then is:

$$u(r,t) = \frac{u_o \exp(-r^2/4Dt - \mu_a ct)}{(4\pi Dt)^{3/2} \cdot [1 - h\sqrt{\pi Dt}\, erfc(h\sqrt{Dt})\exp(h^2 Dt)]}. \quad (11)$$

When the photon current was measured, the source and detector were located at the surface separated by several distinct distances r, and analysis yielded fits for the parameter h, in addition to D and $\mu_a$.

Figure 7:
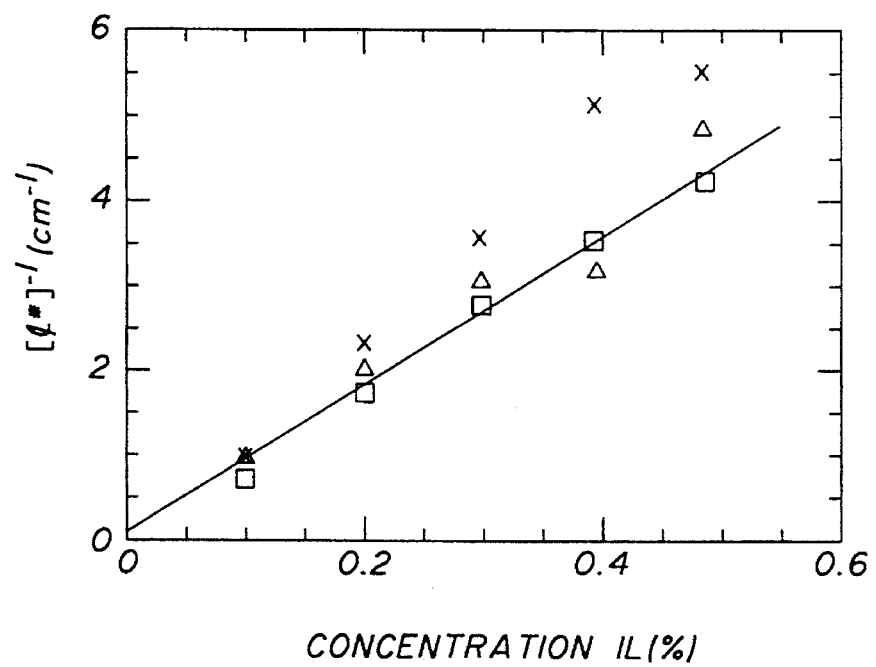
FIG. 7 is a graph of the reciprocal of the mean free path of photons for different concentrations of intralipid scatterers wherein squares represent fits to bulk transmission, stars represent first to surface using pure absorbing boundary conditions, and triangles represent fits using mixed boundary conditions. The solid line is the best fit with respect to bulk transmission data (squares).

Referring to FIG. 7, the mean free path obtained from a surface backscattering data fit (triangles) was compared to the mean free path obtained in the infinite volume case (squares). The agreement between the two data sets is significantly better than that afforded by the assumption of pure absorption boundary conditions.

Figure 8:
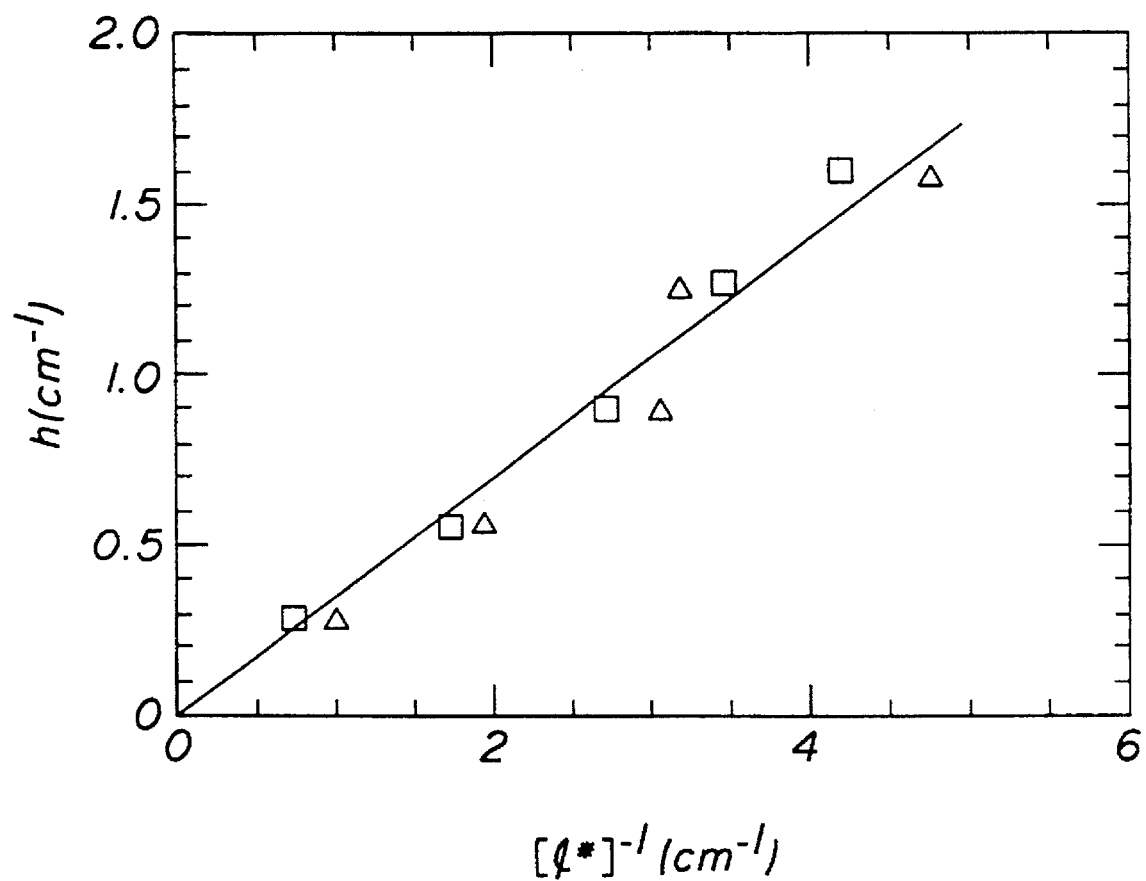
FIG. 8 is a graph of the boundary value parameter, h, for different reciprocal values of the photon mean free path where squares represent the bulk transmission case and triangles represent the backscattering case.

Referring now to FIG. 8, the value of h measured for different concentrations of scatterers is plotted. The parameter h scales with 1/l* as predicted.

It can thus be seen that the diffusion imaging methods, techniques, and apparatus described above produce high quality images of light scattering objects. Systems and methods provided in accordance with the present invention have particularly strong applications in biological and medical imaging where non-invasive approaches are preferred. Furthermore, by taking into account the source-detector orientation as well as boundary conditions and interfaces, objects in inhomogeneous media can be clearly and accurately imaged. Such results have not heretofore been achieved in the art and promise to provide worthwhile and efficient techniques in medical or biological imaging for clinical and diagnostic purposes.

There have thus been described certain preferred embodiments of methods and apparatus for diffusion imaging provided in accordance with the present invention. While preferred embodiments have been described and disclosed, it will be recognized by those with skill in the art that modifications of the methods and apparatus are within the true spirit and scope of the invention. The appended claims are intended to cover all such modifications.

What is claimed is:

1. A method of imaging an object with diffuse light comprising the steps of:

illuminating the object with a source of light which can be scattered by the object;

collecting the scattered light with a detector from multiple positions surrounding the object;

determining a diffusion constant for the photons scattered from the object as a function of the measured mean free path; and determining a net transmission of the photons between the source and the detector as a function of the orientation of the detector with respect to the source and photon flux, thereby imaging the object.

2. The method recited in claim 1 further comprising the step of determining boundary conditions for the photons as the photons traverse a medium between the source and the detector.

3. The method recited in claim 2 wherein the step of determining the net transmission of photons comprises the steps of:

measuring a mean free path of photons scattered from the object from the collected scattered light;

calculating a hitting density for the photons between the source and the detector;

measuring a flux ratio of the photons detected by the detector; and reconstructing an image of the object by deconvolving the hitting density from the measured flux ratio.

4. The method recited in claim 1 further comprising the step of measuring an absorption constant for the photons as they traverse a medium between the source and the detector.

5. The method recited in claim 4 further comprising the step of measuring boundary conditions for the photons as the photons traverse through the medium.

6. The method recited in claim 5 further comprising the step of determining an orientation of the detector with respect to the source to determine a photon current detected by the detector.

7. The method recited in claim 6 further comprising the step of determining a hitting density for the photons between the source and the detector.

8. A system for imaging an object with diffuse light comprising:

a source which produces light to be scattered by the object;

a detector for measuring light emitted from the source and scattered by the object; and processing means interfaced with the detector for determining net transmission of photons scattered from the object and detected by the detector as a function of the orientation of the detector with respect to the source and photon flux, the processing means adapted to determine the net transmission as a function of a probability of photons hitting the detector after being scattered by the body.

9. The system recited in claim 8 wherein the detector is oriented at a known angle with respect to the source.

10. The system recited in claim 9 wherein the source is a laser.

11. The system recited in claim 10 wherein the processing means determines the net transmission by calculating a hitting density for the photons between the source and the detector, measuring a flux ratio of the photons detected by the detector, and reconstructing an image of the object by deconvolving the hitting density from the measured flux ratio.

12. A method of imaging an object with diffuse light comprising the steps of:

illuminating the object with a source of light which can be scattered by the object;

collecting the scattered light from multiple positions surrounding the object with a detector that is oriented at angle with respect to the source;

measuring a mean free path of photons scattered from the object from the collected scattered light;

determining a diffusion constant for the photons scattered from the object as a function of the measured mean free path; and determining a net transmission of the photons between the source and the detector as a function of the diffusion constant and the orientation of the detector with respect to the source and photon flux, thereby imaging the object.

13. The system recited in claim 12 wherein the detector is oriented at a angle with respect to the source.

14. The method recited in claim 13 further comprising the step of determining boundary conditions for the photons as the photons traverse a medium between the source and the detector.

15. The method recited in claim 14 wherein the step of determining the net transmission of photons comprises the steps of:

calculating a hitting density for the photons between the source and the detector;

measuring a flux ratio of the photons detected by the detector; and reconstructing an image of the object by deconvolving the hitting density and the measured flux ratio.

16. The method recited in claim 13 further comprising the step of measuring an absorption constant for the photons as they traverse a medium between the source and the detector.

17. The method recited in claim 16 further comprising the step of measuring boundary conditions for the photons as the photons traverse through the medium.

18. The method recited in claim 17 further comprising the step of determining an orientation of the detector with respect to the source to determine a photon current detected by the detector.

19. The method recited in claim 18 further comprising the step of determining a hitting density for the photons between the source and the detector.

* * * * *